US010354189B2

(12) United States Patent
Volkov

(10) Patent No.: US 10,354,189 B2
(45) Date of Patent: Jul. 16, 2019

(54) ELECTROPHYSIOLOGICAL DETECTION SYSTEMS AND METHODS

(71) Applicant: Bioelectrochemistry, LLC, Madison, AL (US)

(72) Inventor: Alexandre G. Volkov, Huntsville, AL (US)

(73) Assignee: Bioelectrochemistry, LLC, Madison, AL (US)

( * ) Notice: Subject to any disclaimer, the term of this patent is extended or adjusted under 35 U.S.C. 154(b) by 0 days.

(21) Appl. No.: 14/275,416

(22) Filed: May 12, 2014

(65) Prior Publication Data

US 2014/0337270 A1 Nov. 13, 2014

Related U.S. Application Data

(60) Provisional application No. 61/822,572, filed on May 13, 2013, provisional application No. 61/822,038, filed on May 10, 2013.

(51) Int. Cl.
*G06N 5/04* (2006.01)
*G01N 27/30* (2006.01)
*A01G 22/00* (2018.01)
*A01H 5/08* (2018.01)
*A01H 6/78* (2018.01)

(52) U.S. Cl.
CPC ............... *G06N 5/04* (2013.01); *A01G 22/00* (2018.02); *G01N 27/30* (2013.01); *A01H 5/08* (2013.01); *A01H 6/78* (2018.05)

(58) Field of Classification Search
CPC .................................. G06N 5/04; A01G 22/00
See application file for complete search history.

(56) References Cited

U.S. PATENT DOCUMENTS

| 4,975,581 A * | 12/1990 | Robinson | A61B 5/14532 250/339.09 |
|---|---|---|---|
| 2009/0104596 A1* | 4/2009 | Assadi-Porter | C12Q 1/6883 435/5 |
| 2009/0198448 A1* | 8/2009 | Volkov | G01V 1/18 702/15 |
| 2009/0278555 A1* | 11/2009 | Osypka | A01G 7/00 324/692 |

(Continued)

OTHER PUBLICATIONS

Yang, H. Y., and H. Y. Yu. "Study on chlorophyll fluorescence spectrum in the application of the BP-ANN for diagnosing cucumber diseases and insect pests." Journal of FoodAgriculture &Environment 10.1 (2012): 563-566.*

(Continued)

*Primary Examiner* — Scott A. Waldron
*Assistant Examiner* — Kevin W Figueroa
(74) *Attorney, Agent, or Firm* — Dennen IP Law, LLC

(57) ABSTRACT

A system in accordance with an embodiment of the present disclosure comprises at least two electrodes communicatively coupled to a bio-organism. The system further comprises a data acquisition device coupled to the electrodes for receiving analog signals indicative of voltage potential differences in the bio-organism. In addition, the system comprises logic configured to compare a fast Fourier transform (FFT) signature of the signals received with an FFT signature of a bio-organism known to be healthy to determine whether the bio-organism has a particular disease.

6 Claims, 16 Drawing Sheets

(56) References Cited

U.S. PATENT DOCUMENTS

2012/0086502 A1* 4/2012 Smith .................. G01N 33/007
　　　　　　　　　　　　　　　　　　　　327/530

OTHER PUBLICATIONS

Acharya, U. Rajendra, et al. "Automatic identification of cardiac health using modeling techniques: A comparative study." Information Sciences 178.23 (2008): 4571-4582. (Year: 2008).*

* cited by examiner

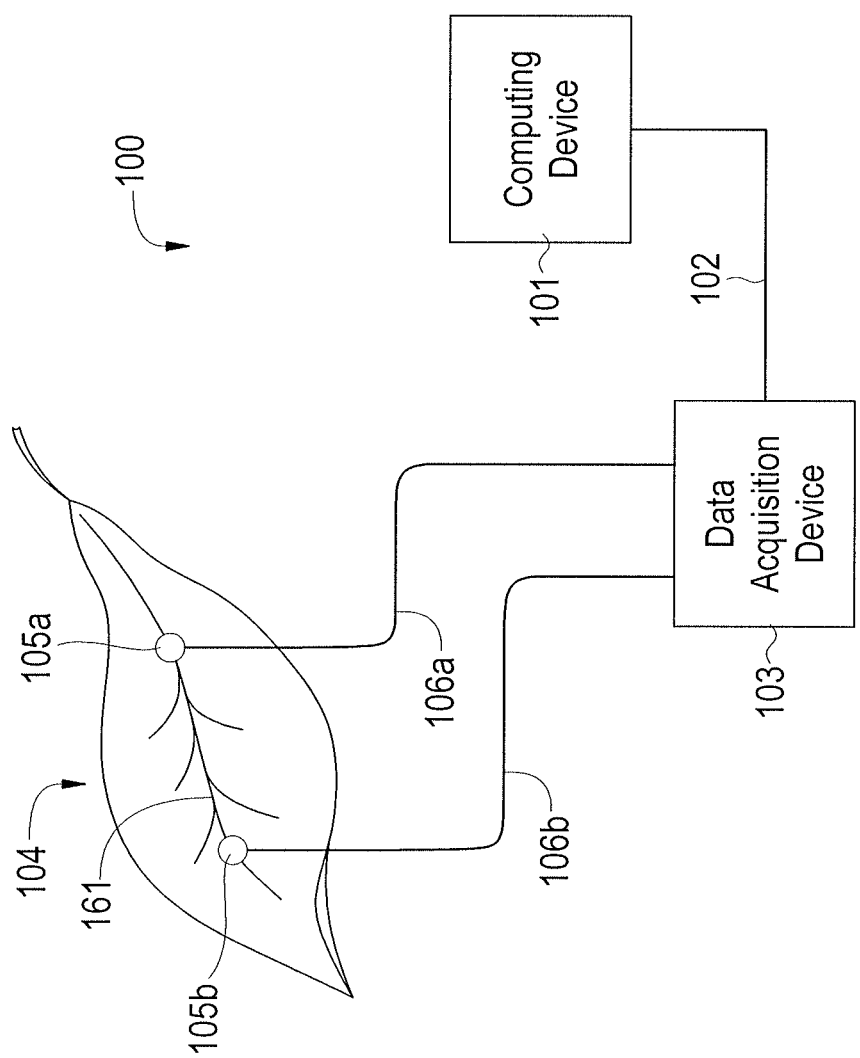

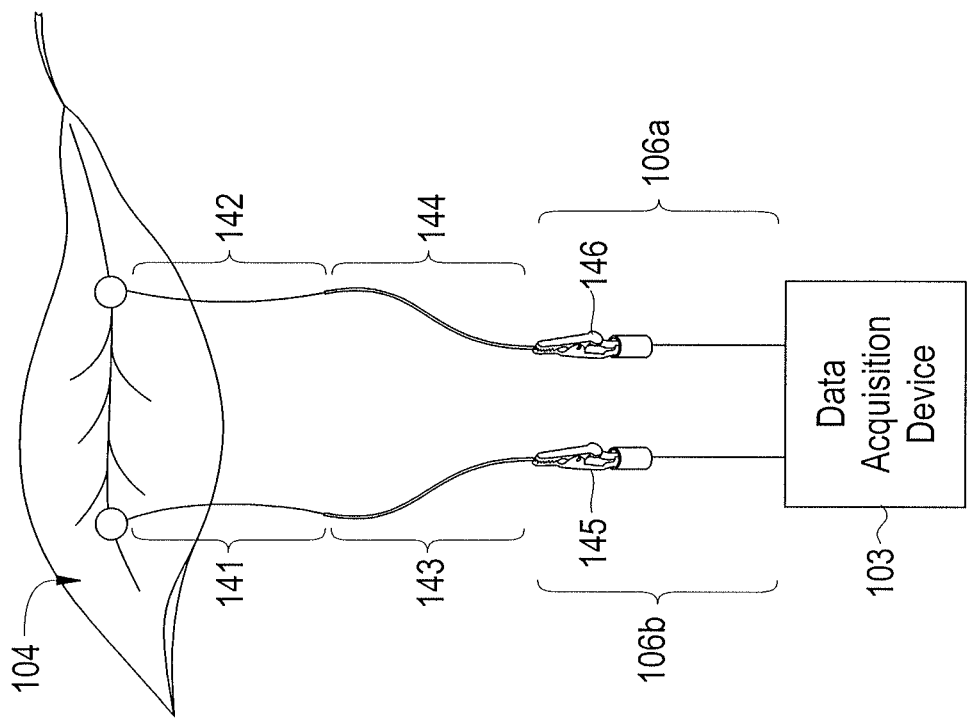

ELECTROPHYSIOLOGICAL DETECTION SYSTEMS AND METHODS

CROSS-REFERENCE

This application claims priority to U.S. Provisional Application No. 61/822,572, entitled "Electrophysiological Detection Systems and Methods" filed on May 13, 2013 and U.S Provisional Patent Application Ser. No. 61/822,038, entitled "Electrophysiological Detection Systems and Methods" filed on May 10, 2013, both of which are incorporated herein by reference.

BACKGROUND OF THE INVENTION

There are a number of diseases that can affect trees and plants. In particular, there are some diseases that affect entire groves of fruit trees, for example. The diseases significantly reduce citrus production in those geographical areas conducive for citrus production, including Florida, Brazil, Asia, and Africa.

One type of disease that affects fruit trees is Citrus Greening Disease (also referred to as Huanglongbing (HLB)). In this regard, Citrus Greening Disease causes disorder in the tree's vascular tissue that conducts sugar and other metabolic products downward through the trunks from the leaves.

Another type of disease that affects citrus trees is Gummosis. Gummosis is a disease that causes copious production and exudation of gum from the infected tree. Thus, gum formation on the trunk or branches of an infected tree is a characteristic symptom of Gummosis, as are cankers the gum flows from.

Electrical phenomena in trees have attracted researches for many years. In this regard, trees typically generate electric potentials that result in a flow of electrical current, and electrical response impulses may be detected as a result of stimulation of the tree.

Detection of diseases in trees is not an easy task until that time the infected trees begin to show external symptoms or characteristics of the disease. In regards to both Citrus Greening Disease and Gummosis, the earlier an infection is detected, the more likely a grove manager can prevent spread of the diseases to other trees in the grove. In this regard, if detection is delayed until symptoms are noticed, it may be too late to save other trees in the grove.

SUMMARY

A system in accordance with an embodiment of the present disclosure has a data acquisition device communicatively coupled to a bio-organism, the data acquisition device receives voltage potential differences over a period of time measured from the bio-organism and transmits data indicative of the voltage potential differences to a computing device. In addition, the system has logic that receives the data indicative of the voltage potential differences and applies a fast Fourier transform (FFT) technique to the received data to obtain FFT test data. Further, the logic compares the FFT test data to pre-stored FFT signature data to determine whether the bio-organism is healthy.

A method in accordance with an embodiment of the present disclosure comprises the following steps: (1) communicatively coupling a data acquisition device to a bio-organism; (2) receiving voltage potential differences over a period of time measured from the bio-organism; (3) transmitting data indicative of the voltage potential differences to a computing device; (4) receiving the data indicative of the voltage potential differences; (5) applying a fast Fourier transform (FFT) technique to the received data to obtain FFT test data; and (6) comparing the FFT test data to pre-stored FFT signature data to determine whether the bio-organism is healthy.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the figures.

FIG. 1A depicts an electrophysiological detection system in accordance with an embodiment of the present disclosure.

FIG. 1C is an exemplary electrode as depicted in FIGS. 1A, 1B.

DESCRIPTION

Figure 1B:
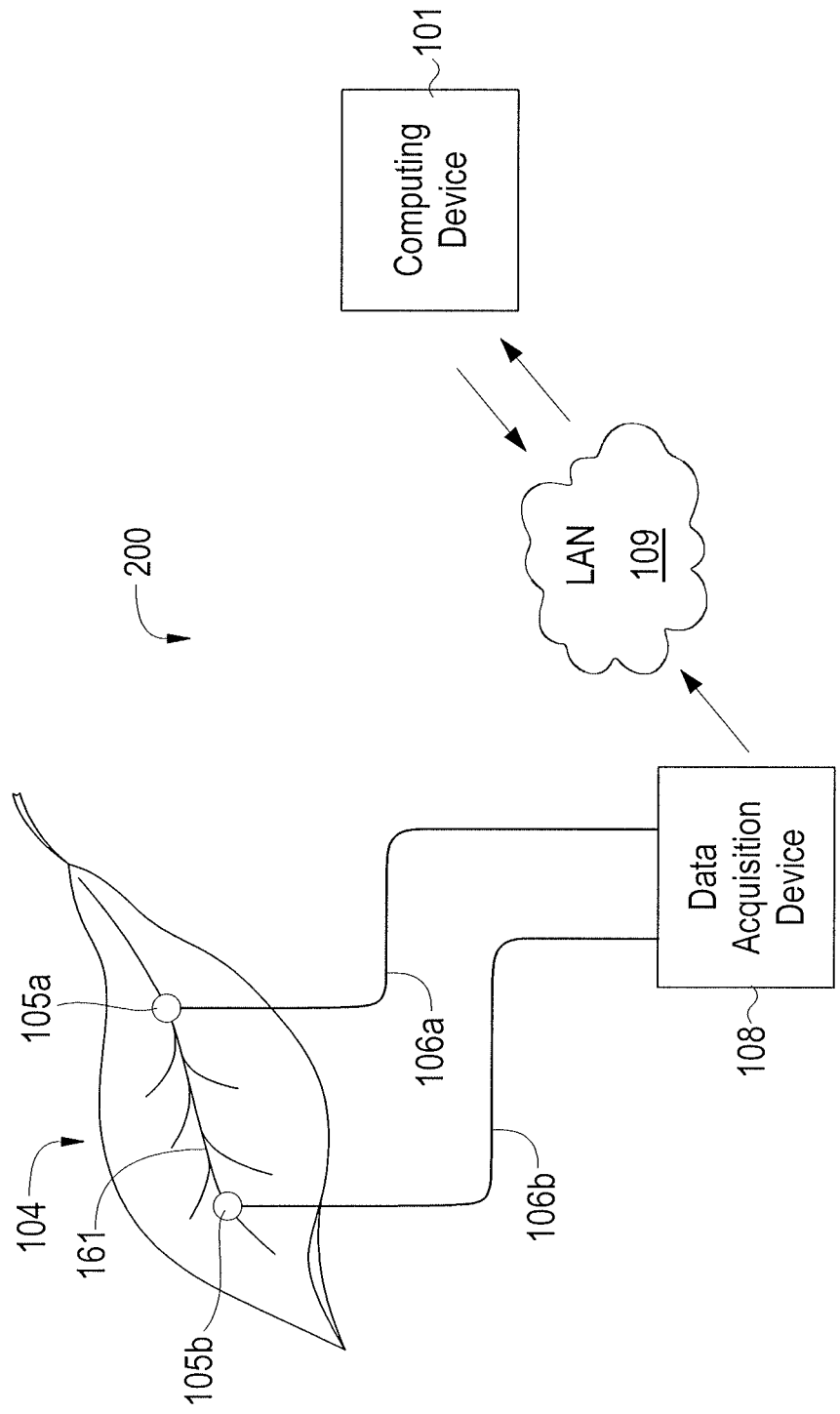
FIG. 1B depicts an electrophysiological detection system in accordance with another embodiment of the present disclosure.

FIG. 1A depicts an electrophysiological detection system 100 in accordance with an embodiment of the present disclosure. The system 100 comprises a data acquisition device 103 that is communicatively coupled via a communication line 102 to a computing device 101.

The data acquisition device 103 comprises two electrical wires 106a, 106b. The wires 106a, 106b are coupled to two electrodes 105a, 105b, respectively.

The data acquisition device 103 receives analog signals from the leaf 105 via the electrodes 10a, 105b and wires 106a, 106b. In this regard, the cells (not shown) of the leaf 104 generate electric potentials that result in the flow of electrical currents. Notably, a leaf may also be electrically stimulated via an external source; however, for purposes of the present disclosure, no stimulation is induced.

As shall be described further herein, the potential difference between the electrodes 105a, 105b is measureable. Further, the voltage potential differences measured in the leaf 104 when the leaf 104 is part of a healthy organism differs from the voltage potential differences measured in the leaf 104 when the leaf is part of an unhealthy organism.

Upon receipt of the analog signals indicative of the potential differences measured in the leaf 104, the data acquisition device 103 transmits data indicative of the analog signals to the computing device 101, via a cable 102.

FIG. 1B depicts an electrophysiological detection system 200 in accordance with another embodiment of the present disclosure. The system 200 comprises a data acquisition device 108 that is similar to data acquisition device 103 except as described further herein. In this regard, the data acquisition device 108 is wirelessly communicatively coupled via a local area network (LAN) 109 to the computing device 101.

Similar to data acquisition device 103, the data acquisition device 108 comprises two electrical wires 106a, 106b. The wires 106a, 106b are coupled to two electrodes 105a, 105b, respectively.

With reference to FIG. 1C, in one embodiment, the data acquisition devices 103 or 108 may comprise the two wires 106a, 106b that terminate with alligator connectors 145, 146, respectively. The alligator connectors 145, 146 couple to silver (Ag) conducting wires 143, 144, respectively. The silver conducting wires 143, 144 terminate in chloride-treated wires ends 141, 142, (hereinafter referred to as "AgCl electrodes") respectively that serve as the electrodes 105a, 105b (FIG. 1A).

In one embodiment, the Ag/AgCl electrodes 141, 142 are Teflon-coated silver wires prepared by electrolysis in 0.05 Moles Potassium Chloride (M KCl) aqueous solution. In such an embodiment, the anode was a high-purity silver wires and the cathode was a platinum plate. Electrical current in the electrolytic cell was limited to 1 milliamp/centimeter2 (mA/cm2) of the anode surface. Stabilization of electrodes was accomplished by placing two Ag/AgCl electrodes in 0.05 M KCl solution for a twenty-four hour period and connecting a short circuit between them. In such a scenario, the resistance between the two Ag/AgCl electrodes was 10 kilo ohms (kΩ), and the response time of the AgCl electrodes 141, 142 was less than 0.1 microsecond (μs) when inserted in the leaf 104 along the vein 161 (FIG. 1A, 1B).

FIG. 1C is merely an exemplary structures for conductively coupling the data acquisition device 103 to the leaf 104. Other structures and/or methods may be used in other embodiments of the present disclosure. Furthermore, data acquisition device 108 (FIG. 1B) may also be coupled to the leaf 104 as described with reference to FIG. 1C.

Figure 2:
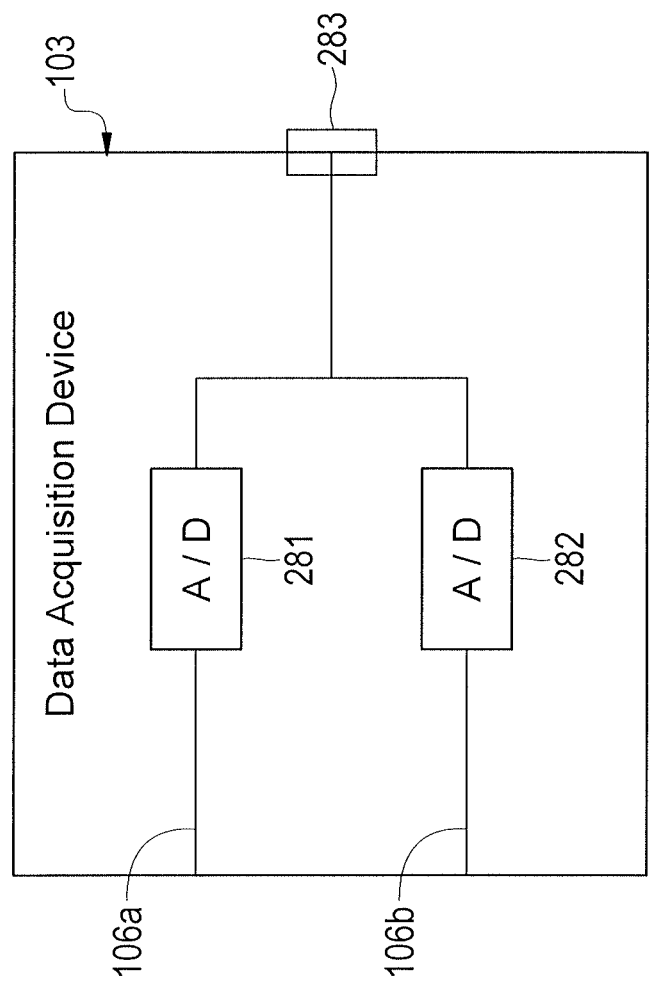
FIG. 2 is a block diagram of an exemplary data acquisition device such as is depicted in FIG. 1A.

With reference to FIG. 2, the data acquisition device 103 comprises two analog-to-digital (A/D) converters 281, 282 that receive the analog signals via the wires 106a, 106b, respectively. The A/D converters 281, 282 convert the analog signals received into digital data representative of the analog signals, and transmit the digital data through a serial port 283 that is connected to cable 102.

Note that when electrochemical potential differences are being measured, a sampling rate is employed by the data acquisition device 103, which determines how often the measurement device samples the received analog signals. In one embodiment, the sampling rate employed by the data acquisition device 103 is 250 kilosamples/second (kS/s).

Figure 3:
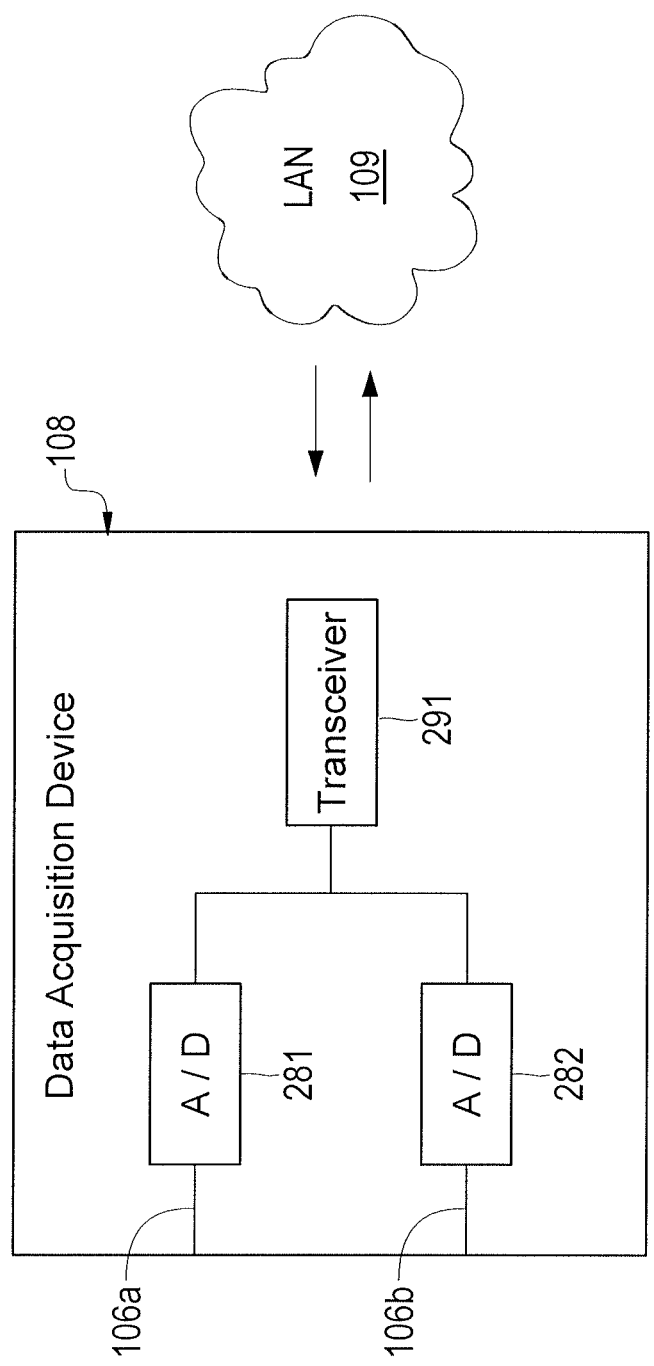
FIG. 3 is a block diagram of an exemplary data acquisition device such as is depicted in FIG. 1B.

Note that similar structure may be employed in the data acquisition device 108 and behave similarly as described with reference to data acquisition device 108. FIG. 3 depicts an exemplary data acquisition device 108. Similar to data acquisition device 103, the data acquisition device 108 comprises the two A/D converters 281, 282 that receive analog signals via the wires 106a, 106b, respectively from the leaf 104 (FIG. 1B). The A/D converters 281, 282 convert the analog signals to digital data. However, dissimilarly to data acquisition device 103, the data acquisition device 108 transmits digital data indicative of the analog signals to the computing device 101 (FIG. 1B) via a wireless transceiver 291 via the LAN 109.

Figure 4:
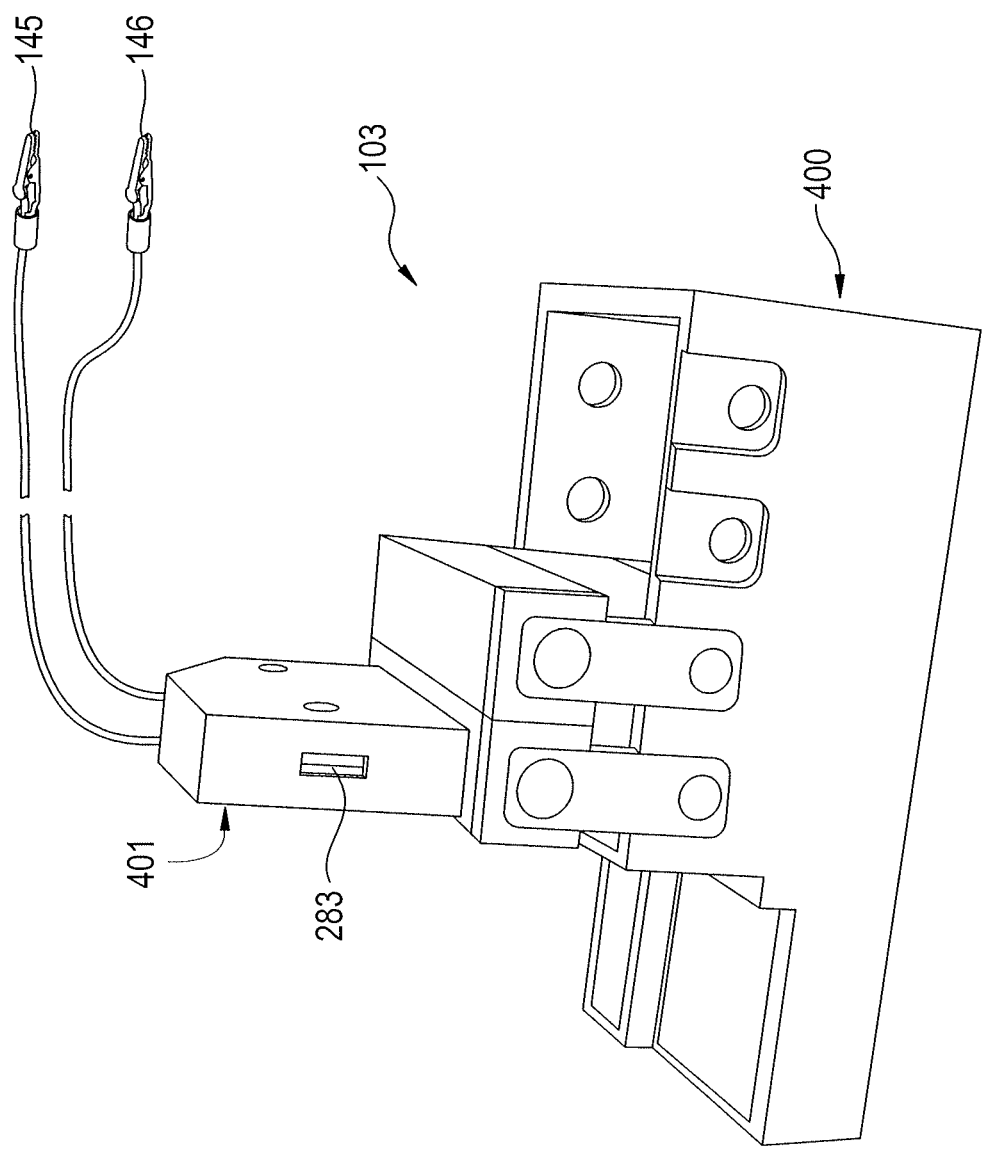
FIG. 4 is a perspective view of an exemplary data acquisition device such as is depicted in FIG. 1A.

FIG. 4 depicts an exemplary data acquisition device 103. The data acquisition device 103 comprises a chassis 400. Inserted in the chassis 400 is a data acquisition card 401. As noted hereinabove with reference to FIG. 2, the data acquisition card 401 in the exemplary embodiment comprises at least two A/D converters 281, 282 (FIG. 2) communicatively coupled to the universal serial bus (USB) 283.

Note that FIG. 4 depicts an exemplary data acquisition device 103. Other types of data acquisition devices may be used in other embodiments.

Figure 5:
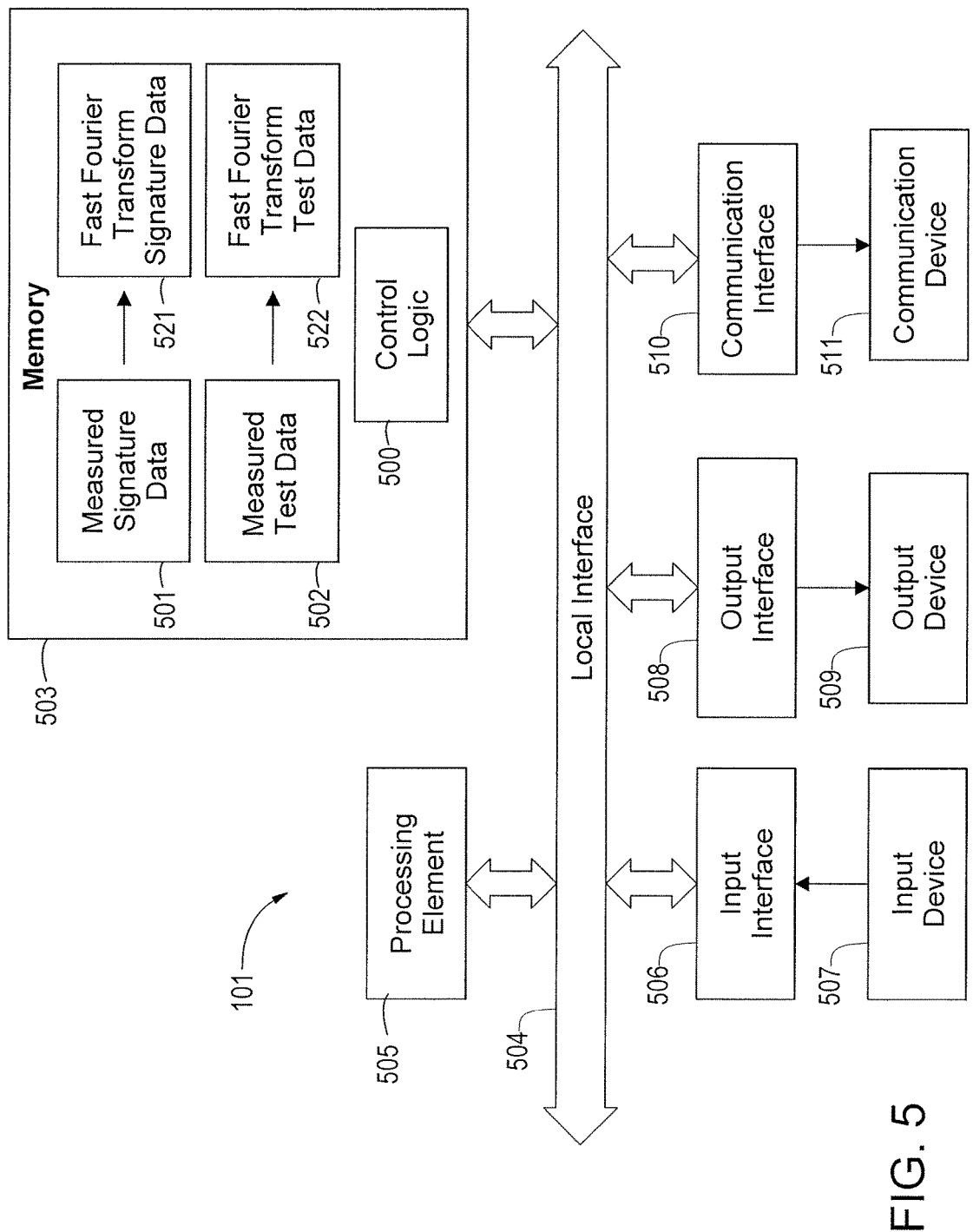
FIG. 5 is a block diagram of a computing device such as is depicted in FIGS. 1A, 1B.

FIG. 5 depicts an exemplary embodiment of the computing device 101 depicted in FIGS. 1A, 1B. As shown by FIG. 5, the computing device 101 comprises control logic 500, measured signature data 501 and measured test data 502 all stored in memory 503. In addition, fast Fourier transform of measured signature data 521 and fast Fourier transform of measured test data 522 are stored in memory 503.

The control logic 500 controls the functionality of the computing device 101, as will be described in more detail hereafter. It should be noted that the control logic 500 can be implemented in software, hardware, firmware or any combination thereof. In an exemplary embodiment illustrated in FIG. 5, the control logic 500 is implemented in software and stored in memory 503.

Note that the control logic 500, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

The exemplary embodiment of the computing device 101 depicted by FIG. 5 comprises at least one conventional processing element 505, such as a digital signal processor (DSP) or a central processing unit (CPU) that communicates to and drives the other elements within the computing device 101 via a local interface 504, which can include at least one bus. Further, the processing element 505 is configured to execute instructions of software, such as the control logic 500.

An input interface 506 may be communicatively coupled to an input device 507, for example, a keyboard, keypad, or mouse. The input interface 506 may be used to receive signals from the input device 507 indicative of input data from a user of the computing device 101.

Further, an output interface 508 may be communicatively coupled to an output device 509, for example, a printer or display screen (e.g., a liquid crystal display (LCD)). The output interface 508 may be used to transmit signals to the output device 509 indicative of output data to the user.

In addition, a communication interface 510 is communicatively coupled to a communication device 511 that enables the computing device 101 to communicate with the data acquisition device(s) 103 (FIG. 1A) or 108 (FIG. 1B). As an example, the communication device 511 may be a modem or a transceiver that enables the computing device 101 to transmit to and receive data from the data acquisition device(s) 103, 108.

In operation, measured signature data 501 is data indicative of voltage potential differences between electrodes 105a, 105b (FIGS. 1A, 1B). In this regard, the data indicative of the voltage potential differences is received from the data acquisition device 103 (FIG. 1A) or 108 (FIG. 1B), as described hereinabove. The measured signature data 501 is data to which measured test data 502 may be compared. In one embodiment, the measured signature data 501 comprises time domain measurements from control bio-organisms that are known to be healthy and uninfected by disease, or otherwise not undergoing an environmental strain (e.g., wind). The measured signature data 501 is received and stored for translation into the fast Fourier transform signature data 521, described hereinafter, which is then compared with measured test data 502 for diagnostic analysis, which shall be described further herein.

Note that the measured signature data 501 may comprise a plurality of distinct sets of data related to differing bio-organisms. For example, as will be described via illustration further herein, the measured signature data 501 may comprise a set of data indicative of voltage difference potentials over a particular time, e.g., two seconds, for a tangerine tree or a Valencia orange tree. In this regard, there may be a set of data indicative of measurements made from a healthy tree for both the tangerine tree and the Valencia orange tree.

In another embodiment, the measured signature data 501 may represent data obtained from a bio-organism that is known to be infected by a particular disease, e.g., citrus greening or gummosis. In such an embodiment, the measured signature data 501 and resulting FFT signature data 521 may be used to identify a particular disease, as described further herein.

Upon receipt or otherwise in response to a user input via the input device 507, the control logic 500 performs a fast Fourier transform (FFT) of the measured signature data 501 and stores the resulting data as FFT Signature data 521. Note that the FFT performed is per each data set. For example, the control logic 500 performs an FFT on the measured signature data 501 corresponding to the tangerine tree and stores FFT signature data for the data set corresponding to the tangerine tree. Separately, the control logic 500 can perform an FFT on the measured signature data 501 corresponding to a Valencia orange tree and can store FFT signature data for the data set corresponding to the Valencia orange tree.

Note that an FFT is an algorithm known in the art for transforming data in a time domain to a frequency domain. In this regard, the FFT algorithm applied by the control logic 500 converts the data indicative of the sampled voltage potential differences into a combination of sinusoids ordered by their frequencies.

Further note that during the process of sampling and translation to the frequency domain, the control logic 500 may employ a low pass filter. In this regard, in order to avoid aliasing, the control logic 500 may employ a low pass filter to avoid aliasing so that higher frequency components of the original signal are not misrepresented as lower frequencies.

Once the FFT signature data 521 is generated and stored, the FFT signature data 521 is used by the control logic 500 to determine whether a bio-organism is healthy. Additionally, the FFT signature data 521 is used by the control logic 500 to identify what type of disease may be affecting a bio-organism.

In this regard, the data acquisition devices 103 or 108 collect data via electrodes 105a, 105b for a bio-organism, which is received by the control logic 500 and stored as measured test data 502. The measured test data 502, similar to the measured signature data 501, is data indicative of voltage potential differences between electrodes 105a, 105b. However, the measured test data 502 is collected from a non-control bio-organism where the health of the bio-organism is unknown.

The data indicative of the voltage potential differences is received from the data acquisition device 103 or 108, as described hereinabove. The measured test data 502 comprises time domain measurements from the non-control bio-organism. The measured test data 502 is received and stored for translation into the fast FFT data 522, described hereinafter, which is then compared with the FFT signature data 521 for diagnostic analysis, which shall be described further herein.

Note that as described hereinabove, the measured signature data 501 may comprise a plurality of distinct sets of data related to differing bio-organisms. However, based upon user input, the control logic 500 compares the FFT test data 522 corresponding to a particular tree, e.g., tangerine, with the FFT signature data 521 corresponding to that particular tree, e.g., tangerine.

In comparing the FFT test data 522 with the FFT signature data 521 to determine whether a tree under test is diseased, the control logic 500 may determine the statistical likelihood that the FFT test data 522 is substantially similar to the FFT signature data 521 through a correlation or a convolution method.

Note that in one embodiment, the computing device 101 may be a tablet device, such as for example an iPad®. In such an embodiment, the control logic 500 may be an application that runs on the iPpad®, e.g., an "app," that is accessible via selection of an icon displayed to the output device 509. In one embodiment, the control logic 500 implements Labview 8™ for applying Fast Fourier Transforms to the measured signature data 501 and the measured test data 502.

To further illustrate the present disclosure, two examples are hereinafter provided. FIGS. 6A-6D and related disclosure provide an example of using the system of the present disclosure for determining the lack of health in a tangerine tree and identifying gummosis in the tangerine tree. In addition, FIGS. 7A-7D and related disclosure provide an example of using the system of the present disclosure for determining the lack of health in a Valencia orange tree and identifying citrus greening in the Valencia orange tree.

Figure 6A:
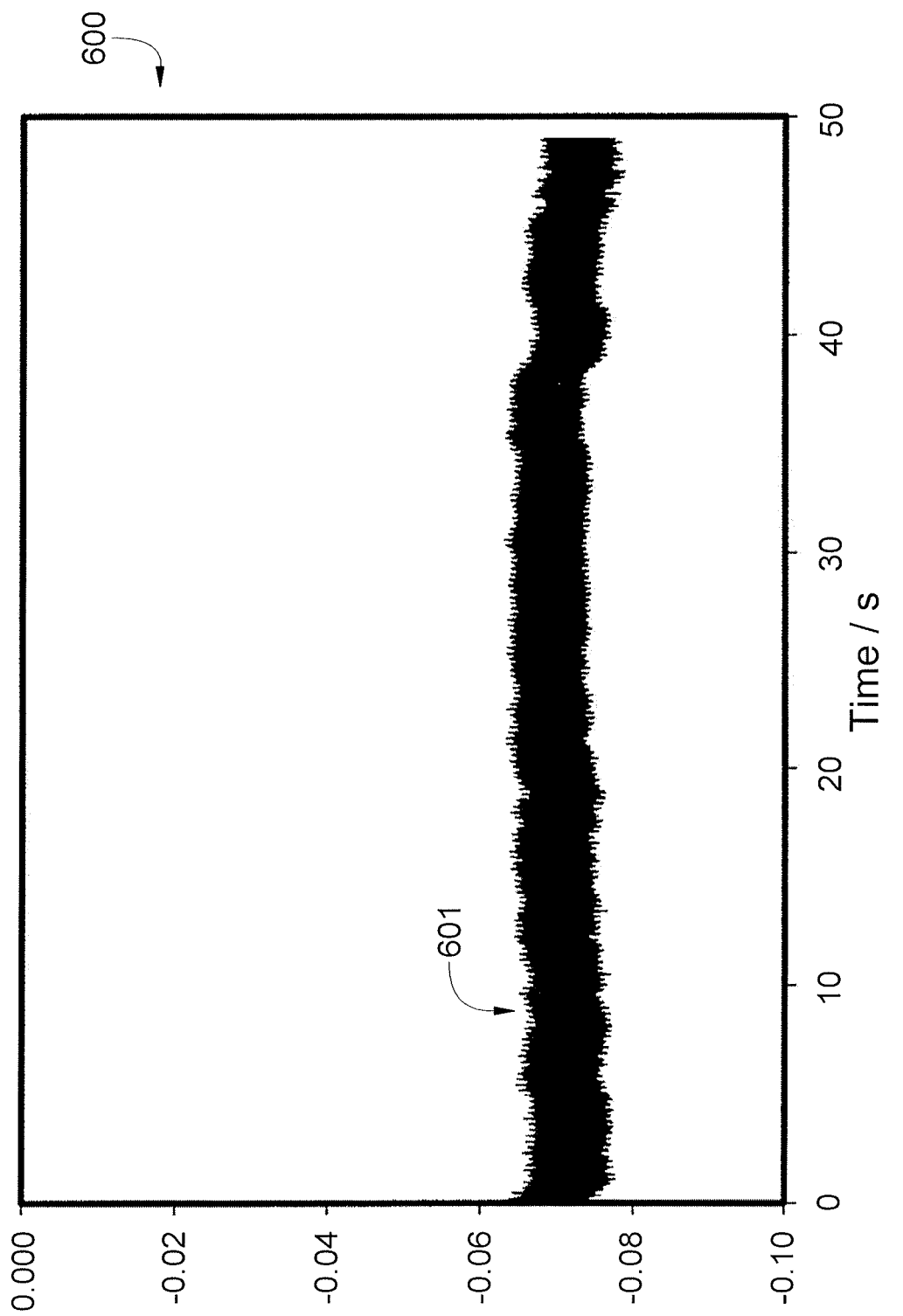
FIG. 6A is a graph depicting data in the time domain of electrode measurements made of a healthy tangerine tree in accordance with an embodiment of the present disclosure.

FIG. 6A depicts a graph 600 of data 601 collected via the data acquisition device 103 (FIG. 1A) from electrodes 105a, 105b placed 5 centimeters (cm) apart on a healthy tangerine leaf. Note that 5 cm is an exemplary separation distance between the electrodes 105a, 105b, and the electrodes 105a, 105b may be placed closer together or farther apart in other embodiments. The vertical axis reflects voltage measurements and the horizontal axis reflects time. Thus, the data 601 shown represents voltage potential differences in the electrodes 105a, 105b over an approximate forty-second interval. The voltage potential differences range from approximately between 0.06 to 0.08 Volts. Note that in the embodiment depicted, the scanning frequency was 50,000 scans per second with a low pass filter at 25,000 scans per second.

The control logic 500 (FIG. 5) receives data 601 illustrated in graph 600 and stores the data 601 as measured signature data 501 (FIG. 5). The received data 601 is in the time domain and represents data from a healthy tangerine tree, which the control logic 500 transforms into the frequency domain as illustrated in FIG. 6C and described further herein.

Figure 6B:
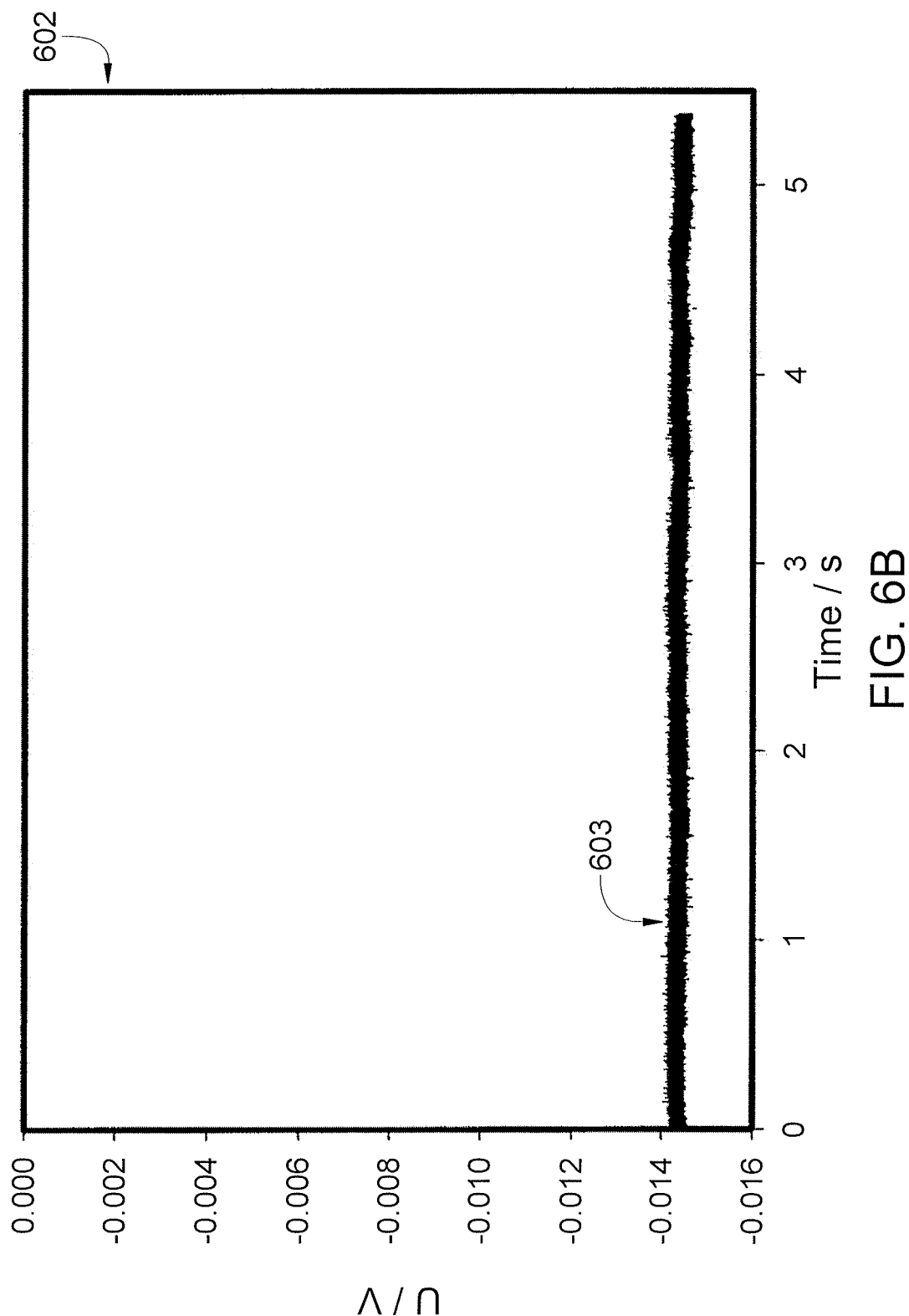
FIG. 6B is a graph depicting data in the time domain of electrode measurements made of a tangerine tree with gummosis in accordance with an embodiment of the present disclosure.

FIG. 6B depicts a graph 602 of data 603 collected via the data acquisition device 103 (FIG. 1A) from electrodes 105a, 105b placed 5 centimeters (cm) apart on a tangerine leaf infected with *Phytophthora* spp (Gummosis). The vertical axis reflects voltage measurements and the horizontal axis reflects time. Thus, the data 603 shown represents voltage potential differences in the electrodes 105a, 105b over an approximate five-second interval. The voltage potential differences range from approximately between 0.015 to 0.014 Volts. Note that in the embodiment depicted, the scanning frequency was 50,000 scans per second with a low pass filter at 25,000 scans per second.

The control logic 500 (FIG. 5) receives the data 603 illustrated in graph 602 and stores the data as measured test data 502 (FIG. 5). The received data 603 is in the time domain and represents data collected from a tangerine tree whose health is unknown. The control logic 500 transforms the data 603 illustrated in graph 602 into the frequency domain as illustrated in FIG. 6D and described further herein.

Figure 6C:
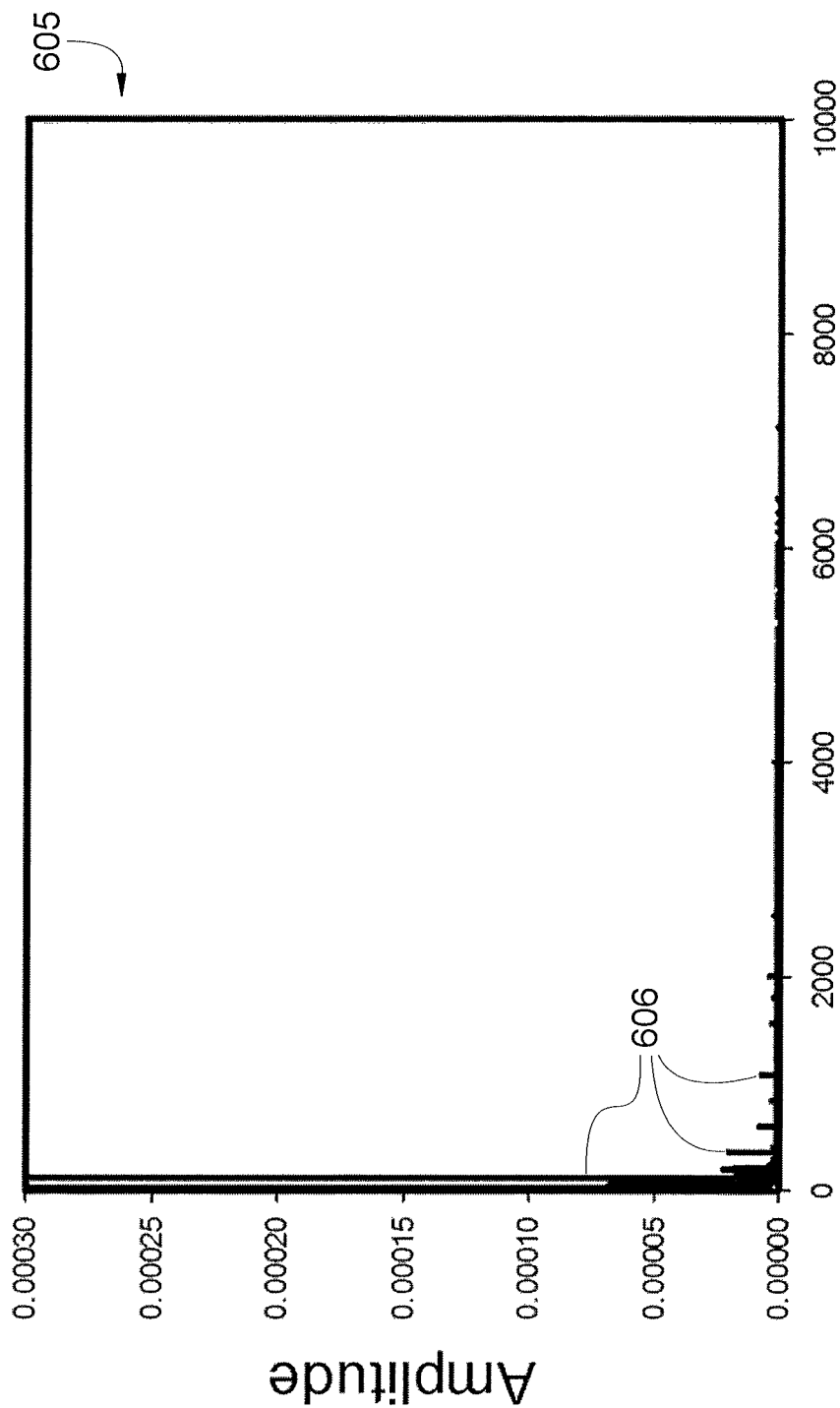
FIG. 6C is a graph depicting the data of FIG. 6A in the frequency domain after application of a fast Fourier transform.

FIG. 6C depicts a graph 605, which represents the data 601 (FIG. 6A) converted to the frequency domain using a fast Fourier transform (FFT). The various spikes 606 depicted in the graph 605 represent an FFT signature of a healthy tangerine leaf, which is stored as FFT signature data 521 (FIG. 5).

Figure 6D:
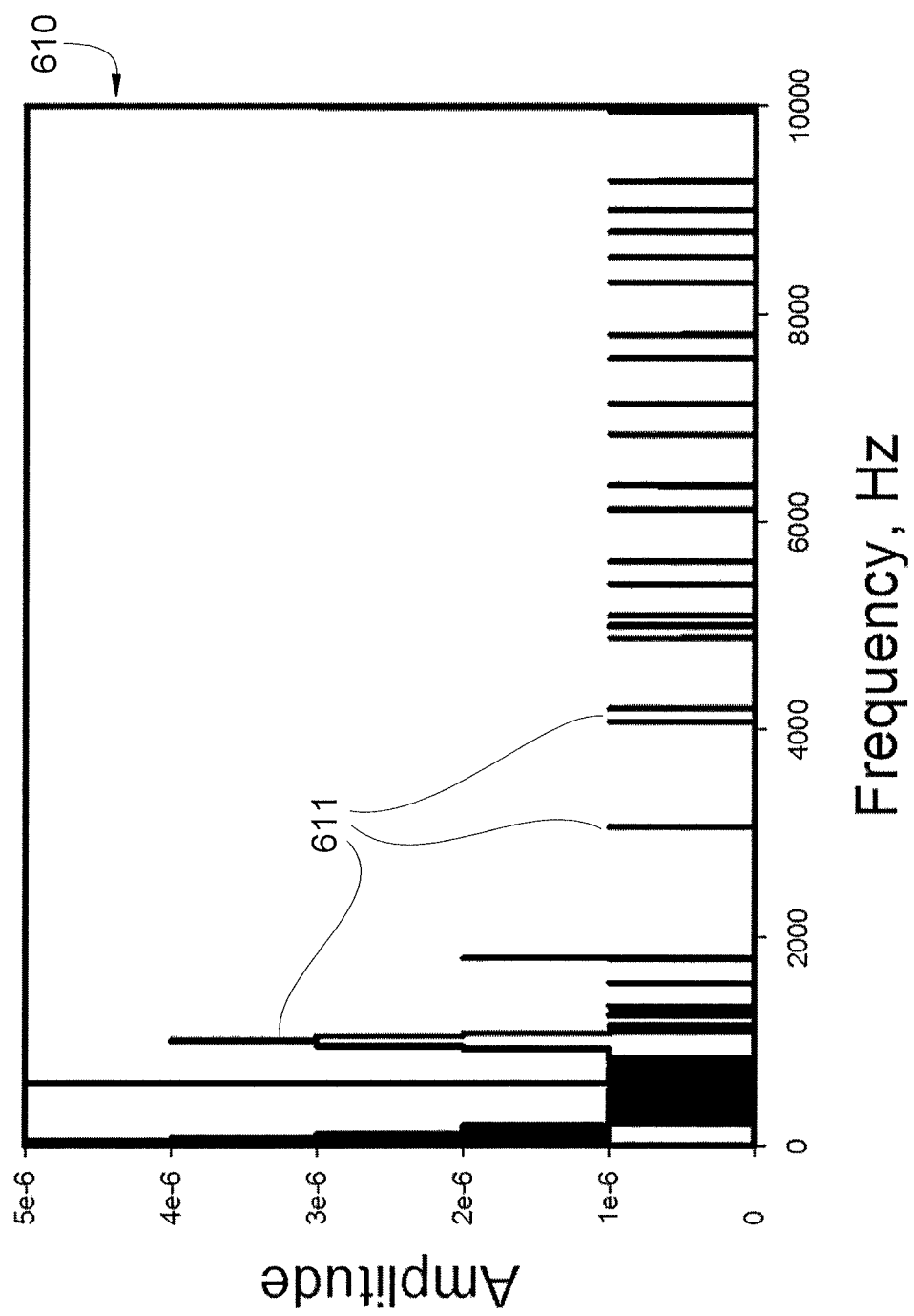
FIG. 6D is a graph depicting the data of FIG. 6B in the frequency domain after application of a fast Fourier transform.

FIG. 6D depicts a graph 610, which represents the data 603 (FIG. 6B) converted to the frequency domain using a fast Fourier transform (FFT). The various spikes 611 depicted in the graph 610 represent an FFT signature of a tangerine leaf from a tree infected with Gummosis, which is stored as FFT test data 522 (FIG. 5)

The control logic 500 compares the FFT signature data 521 depicted in graph 605 with the FFT test data 522 depicted in graph 610. In this regard, FFT test data 522 received from a tree of unknown health may be compared to the FFT signature data 521 for a healthy tree. If there is substantially similarity, the control logic 500 can determine that the tree from which the FFT test data 522 is received is likely healthy.

As described hereinabove, the measured signature data 501 and corresponding FFT signature data 521 may depict data collected from a tree with a known disease, e.g., gummosis. In this regard, measured test data 502 received from a tree of unknown health may be compared to the FFT signature data 521 for the tree known for having gummosis. If there is substantially similarity, the control logic 500 can identify that the tree from which the measured test data 502 is received has a substantial likelihood of having gummosis.

Figure 7A:
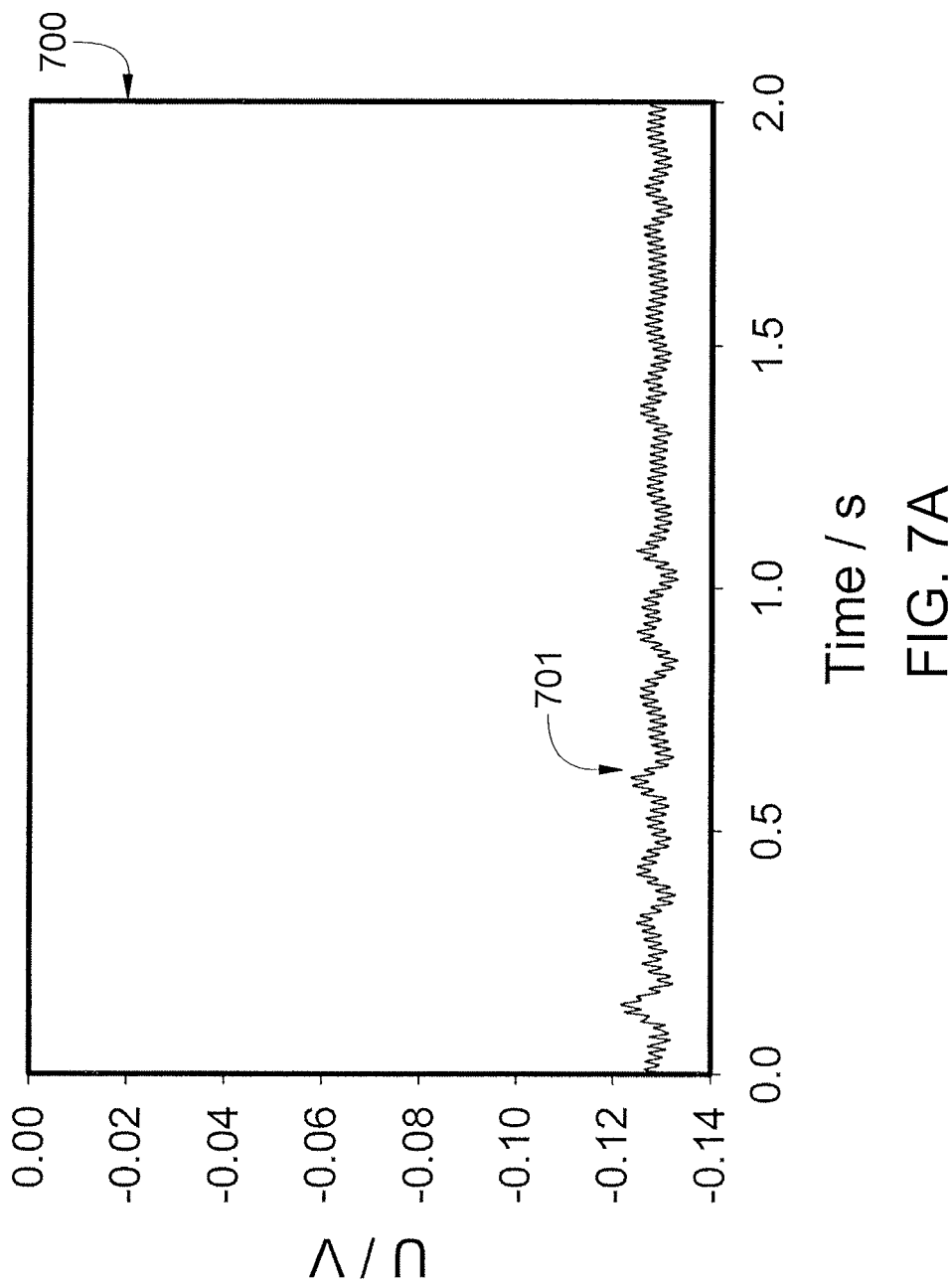
FIG. 7A is a graph depicting data in the time domain of electrode measurements made of a healthy Valencia orange tree in accordance with an embodiment of the present disclosure.

FIG. 7A depicts a graph 700 of data 701 collected via the data acquisition device 103 or 108 from electrodes 105a, 105b placed 5 centimeters (cm) apart on a Valencia orange leaf from a healthy tree. The vertical axis reflects voltage measurements and the horizontal axis reflects time. Thus, the data 701 shown represents voltage potential differences in the electrodes 105a, 105b over an approximately two-second interval. The potential difference readings range from approximately between 0.12 to 0.14 Volts. Note that in the embodiment depicted, the scanning frequency was 50,000 scans per second with a low pass filter at 25,000 scans per second.

The control logic 500 (FIG. 5) receives data illustrated in graph 700 and stores the data as measured signature data 501 (FIG. 5). The received data 701 is in the time domain and represents data from a healthy Valencia orange tree, which the control logic 500 transforms into the frequency domain as illustrated in FIG. 7C and described further herein.

Figure 7B:
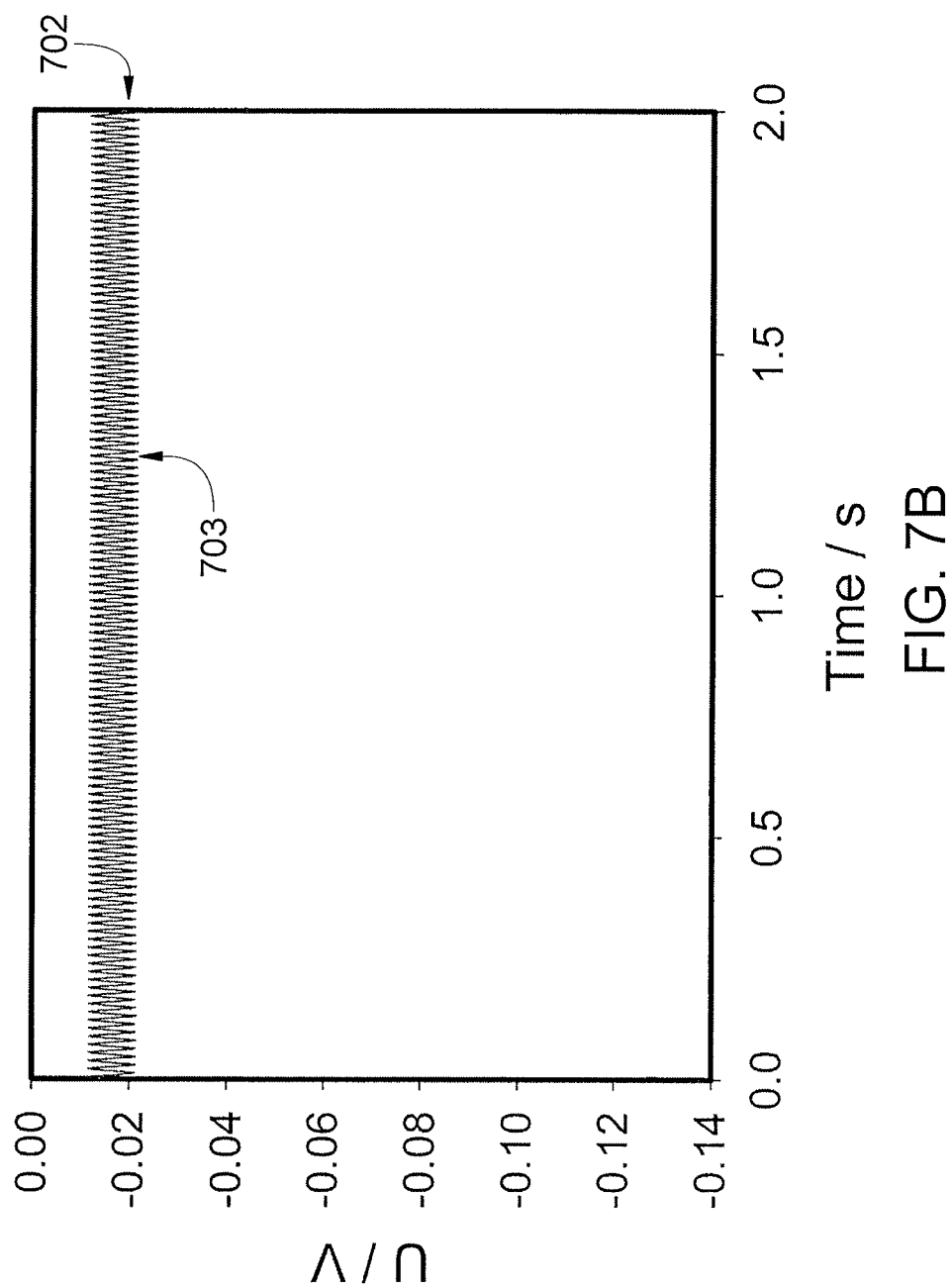
FIG. 7B is a graph depicting data in the time domain of electrode measurements made of a Valencia orange tree with citrus greening in accordance with an embodiment of the present disclosure.

FIG. 7B depicts a graph 702 of data 703 collected via the data acquisition device 103 (FIG. 1A) from electrodes 105a, 105b placed 5 centimeters (cm) apart on a Valencia orange leaf from a tree infected with citrus greening. The vertical axis reflects voltage measurements and the horizontal axis reflects time. Thus, the data 703 shown represents voltage potential differences in the electrodes 105a, 105b over an approximately two-second interval. The voltage potential difference readings range from approximately between 0.01 to 0.01 Volts. Note that in the embodiment depicted, the scanning frequency was 50,000 scans per second with a low pass filter at 25,000 scans per second.

The control logic 500 receives data illustrated in graph 702 and stores the data as measured test data 502 (FIG. 5). The data received is in the time domain and represents data collected from a tangerine tree whose health is unknown. The control logic 500 transforms the data 703 into the frequency domain as illustrated in FIG. 7D and described further herein.

Figure 7C:
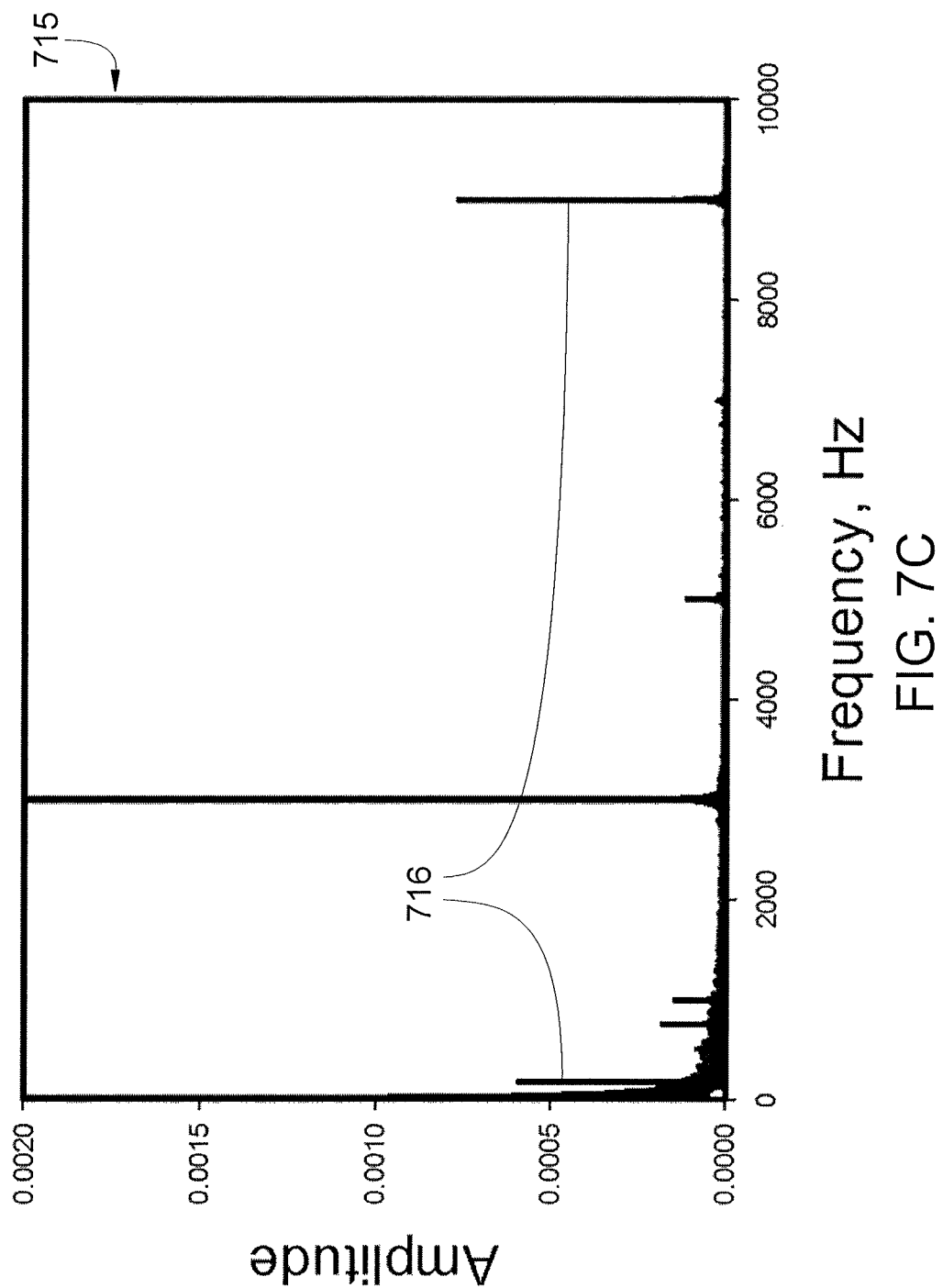
FIG. 7C is a graph depicting the data of FIG. 7A in the frequency domain after application of a fast Fourier transform.

FIG. 7C depicts a graph 715, which represents the data 701 (FIG. 7A) converted to the frequency domain using a fast Fourier transform (FFT). The various spikes 716 depicted in the graph 715 represent an FFT signature of a healthy Valencia orange leaf, which is stored as FFT signature data 521 (FIG. 5).

Figure 7D:
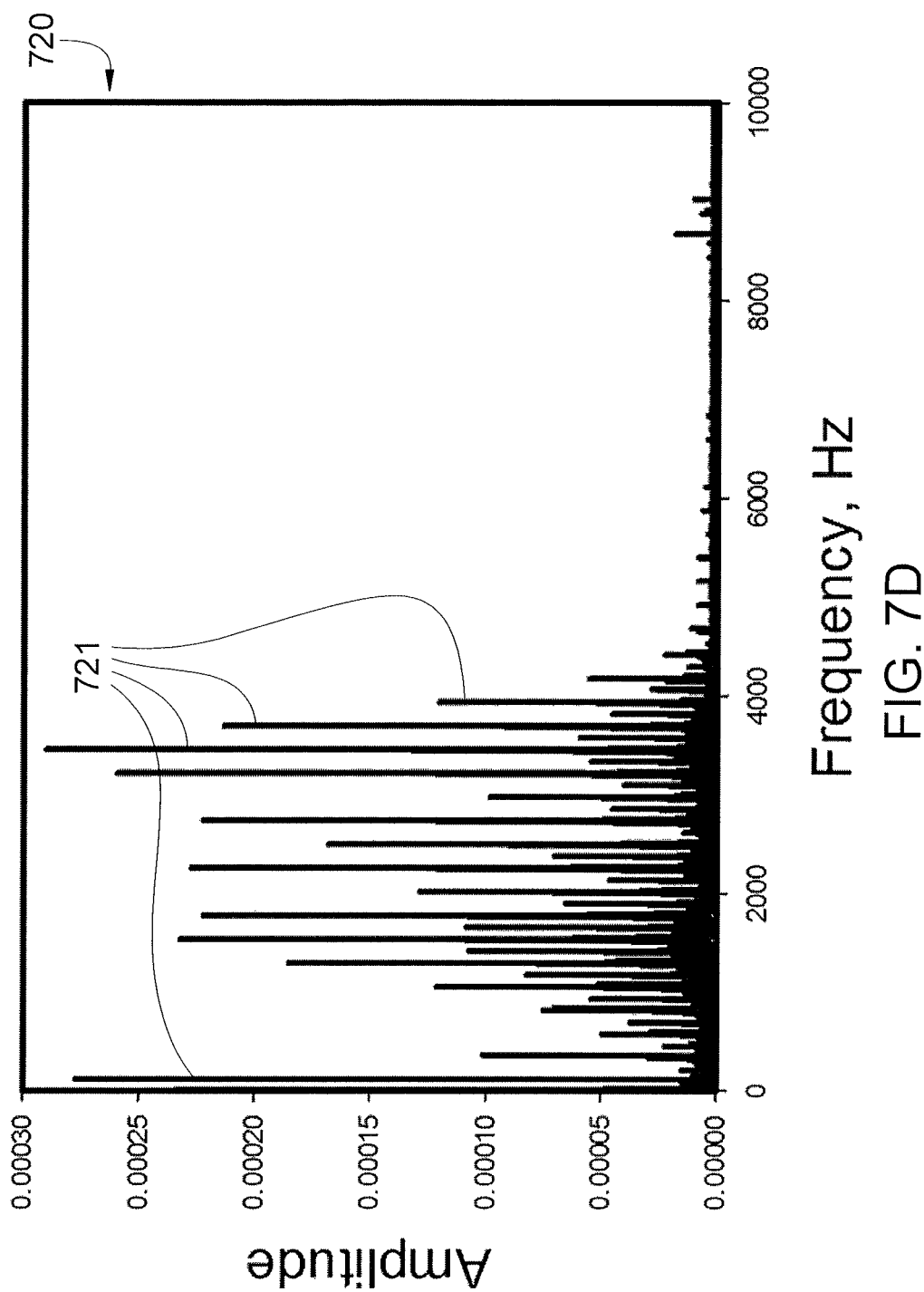
FIG. 7D is a graph depicting the data of FIG. 7B in the frequency domain after application of a fast Fourier transform.

FIG. 7D depicts a graph 720, which represents the data 703 (FIG. 7B) translated to the frequency domain using a fast Fourier transform (FFT). The various spikes 721 depicted in the graph 720 represent an FFT signature of a Valencia orange leaf from a tree infected with citrus greening, which is stored as FFT test data 522 (FIG. 5).

The control logic 500 compares the FFT signature data 521 depicted in graph 715 with the FFT test data 522 depicted in graph 720. In this regard, FFT test data 522 received from a tree of unknown health may be compared to the FFT signature data 521 for a healthy tree. If there is substantially similarity, the control logic 500 can determine that the tree from which the FFT test data 522 is received is likely healthy.

In another embodiment, the measured signature data 501 and corresponding FFT signature data 521 may depict data collected from a tree with a known disease, e.g., citrus greening, such as is depicted in graph 720 of FIG. 7D. In this regard, measured test data 502 received from a tree of unknown health may be compared to the FFT signature data 521 (e.g., the data in graph 720) for the tree known for having citrus greening. If there is substantially similarity, the control logic 500 can identify that the tree from which the measured test data 502 is received has a substantial likelihood of having citrus greening.

Figure 8:
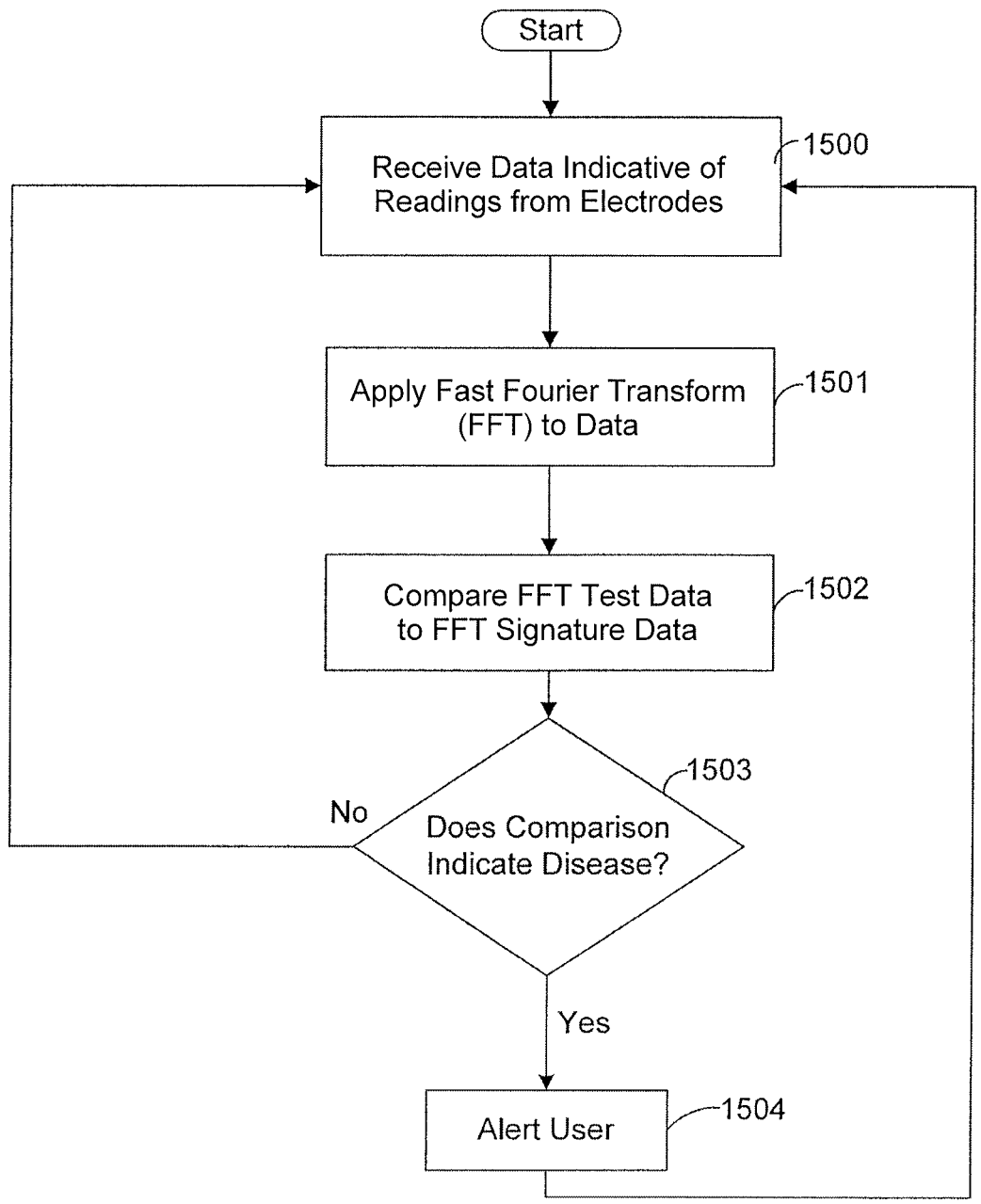
FIG. 8 is a flowchart depicting exemplary architecture and functionality of a system such as is depicted in FIGS. 1A, 1B.

FIG. 8 is a flowchart depicting architecture and functionality of the systems 100, 200 of the present disclosure.

In step 1500, the control logic 500 (FIG. 5) receives data indicative of measurements from electrodes 105*a*, 105*b* (FIG. 1A, 1B). Note that the control logic 500 may receive the data via a USB connector 283 (FIG. 2) or via a transceiver 291 (FIG. 3).

In step 1501, the control logic 500 applies a fast Fourier transform to the data received to obtain the FFT test data 522 (FIG. 5). In step 1502, the control logic 500 compares the FFT test data 522 to a pre-stored FFT signature. As indicated hereinabove, the comparison may be made to FFT signature data 521 indicative of a healthy bio-organism or a bio-organism that has a known particular disease.

If the comparison indicates disease, the control logic 500 alerts a user of the diagnosis, as indicated in step 1504.

What I claim is:

1. A system for detecting health of a plant, the system comprising:
    a healthy plant that is known to not have diseases or stressors, the healthy plant generates electrical signals internally without external stimulation and is coupled to non-polarized silver-silver chloride electrodes;
    a second plant the health of which is unknown that is it is unknown whether the second plant has diseases or stressors, the second plant generates electrical signals internally without external stimulation and is coupled to nonpolarized silver-silver chloride electrodes;
    a data acquisition device communicatively coupled with the non-polarized silver-silver chloride electrodes to the healthy plant, the data acquisition device configured to receive an internally generated alternating current (AC) signal in a time domain generated by the healthy plant which is a signature subset of passive voltage potential differences generated in the healthy plant without external stimulation over a period of time via the non-polarized silver-silver chloride electrodes, the data acquisition device further configured to receive an internally generated AC signal in a time domain from the second plant, the health of which is unknown, which is a signature of a target subset of passive voltage potential differences generated in the second plant without external stimulation over a period of time via the non-polarized silver-silver chloride electrodes, the data acquisition device further configured to transmit data indicative of the AC signals in the time domain of the signature subset and the target subset of voltage potential differences to a computing device;
    a processor on the computing device configured to receive the data indicative of the AC signals of the signature subset and the target subset, the processor further configured to apply a fast Fourier transform (FFT) technique to the signature subset thereby generating a first representative signal in the frequency domain, the first representative signal in the frequency domain comprising a plurality of spikes at particular frequencies and having particular amplitudes, the processor further configured to apply a FFT technique to the target subset thereby generating a second representative signal in the frequency domain, the second representative signal in the frequency domain comprising a plurality of spikes at particular frequencies and having particular amplitudes, the processor further configured to measure the frequencies of the spikes of the first representative signal and measure the frequencies of the spikes of the second representative signal, measure the particular amplitudes of the spikes of the first representative signal and measure the particular amplitudes of the spikes of the second representative signal, and measure the direct current (DC) signal portion of the AC signal generated by the healthy plant and measure the DC signal portion of the AC signal generated by the second plant the health of which is unknown, when at least some of the spikes of the second representative signal are at frequencies different than the spikes of the first representative signal, the amplitudes of the spikes of the second representative signal are more or less than the amplitudes of the first representative signal, and the DC portion of the AC signal of the second plant is less than the DC portion of the AC signal of the healthy plant, the processor determines that the second plant has a disease or a stressor, and when the determination indicates that the second plant has a disease or a stressor, the processor is further configured to measure the spikes of the second representative signal and measure frequencies of spikes of an FFT graph of a plant having a known disease, measure the amplitudes of the spikes of the second representative signal and measure amplitudes of spikes of an FFT graph of the plant having the known disease, and measure the DC portion of the AC signal of the second plant and measure a DC portion of an AC signal of the plant having the known disease, when the location of the spikes of the second representative signal are at substantially similar frequencies of the spikes of the FFT graph of the plant having the known disease, the amplitudes of the spikes of the second representative signal are substantially similar to the amplitudes of the FFT graph of the plant having the known disease, and the DC portion of the AC signal of second plant is substantially similar to the DC portion of the AC signal of the plant having the known disease, the processor determines that the second plant has the known disease; and
    an output device, wherein the processor is configured to output data to an output device that the second plant has a disease and output the type of the known disease the plant is exhibiting so that remedial action can be taken.

2. The system for detecting health of a plant of claim 1, wherein the data acquisition device comprises an analog-to-digital converter for converting analog signals indicative of the voltage potential differences to digital data.

3. The system for detecting health of a plant of claim 1, wherein the processor applies a low pass filter to the received data.

4. A method for detecting health of a plant, the method comprising:
    providing a healthy plant that is known to not have diseases or stressors, the healthy plant generates electrical signals internally without external stimulation and is coupled to silver-silver chloride non-polarized electrodes;
    providing a second plant the health of which is unknown that is it is unknown whether the second plant has diseases or stressors, the second plant generates electrical signals internally without external stimulation and is coupled to silver-silver chloride non-polarized electrodes;
    communicatively coupling a data acquisition device to the healthy plant via the silver-silver chloride non-polarized electrodes;
    receiving an internally generated alternating current (AC) signal generated by the healthy plant which is a signature subset of passive voltage potential differences generated in the healthy plant without stimulation over a period of time;

communicatively coupling the data acquisition device to the second plant via the silver-silver chloride non-polarized electrodes;

receiving an internally generated AC signal in the time domain from the second plant the health of which is unknown, the AC signal is a signature of a target subset of passive voltage potential differences generated in the second plant without stimulation over a period of time;

transmitting data indicative of the AC signals in the time domain of the signature subset and the target subset to a computing device;

receiving, by the computing device, the data indicative of the AC signals in the time domain of the signature subset and the target subset;

applying a fast Fourier transform (FFT) technique to the data indicative of the signature subset thereby generating a first representative signal in the frequency domain, the first representative signal in the frequency domain comprising a plurality of spikes at particular frequencies and having particular amplitudes;

applying an FFT technique to the target subset thereby generating a second representative signal in the frequency domain, the second representative signal in the frequency domain comprising a plurality of spikes at particular frequencies and having particular amplitudes to obtain FFT signature data and FFT target data;

measuring the frequencies of the spikes of the first representative signal and measuring the frequencies of the spikes of the second representative signal;

measuring the particular amplitudes of the spikes of the first representative signal and measuring the particular amplitudes of the spikes of the second representative signal;

measuring the direct current (DC) signal portion of the AC signal generated by the healthy plant and measuring the DC signal portion of the AC signal generated by the second plant the health of which is unknown;

when some of the spikes of the second representative signal are at frequencies different than the spikes of the first representative signal, the amplitudes of the spikes of the second representative signal are more or less than the amplitudes of the first representative signal, and the DC portion of the AC signal of the second plant is less than the DC portion of the AC signal of the healthy plant, determining that the second plant has a disease or stressor based upon the measreuments;

when the measurements indicate that the second plant has a disease or a stressor, measuring the frequencies of the spikes of the second representative signal and measuring frequencies of spikes of a predetermined FFT graph of a plant having a known disease, measuring the amplitudes of the spikes of the second representative signal and measuring amplitudes of the spikes of the FFT graph of the plant having a known disease, and measuring the DC portion of the AC signal of the second plant and measuring a DC portion of an AC signal of the plant having the known disease;

if the frequencies of the spikes of the second representative signal are at substantially similar frequencies of the spikes of the FFT graph of the plant having the known disease, the amplitudes of the spikes of the second representative signal are substantially similar to the amplitudes of the FFT graph of the plant having the known disease, and/or the DC portion of the AC signal of the second plant is substantially similar to the DC portion of the AC signal of the plant having the known disease, determining that the second plant has the known disease; and outputting data to an output device that the second plant has a disease or stressor and the known disease the second plant is exhibiting so that remedial action can be taken.

5. The method for detecting health of a plant of claim 4, further comprising concerting analog signals indicative of the voltage potential differences to digital data.

6. The method for detecting health of a plant of claim 4, further comprising applying a low pass filter to the received data.

* * * * *